(12) United States Patent
Wang et al.

(10) Patent No.: US 12,090,277 B2
(45) Date of Patent: Sep. 17, 2024

(54) VENTILATION APPARATUS

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Hao Wang, Shenzhen (CN); Gang Yao, Shenzhen (CN); Fei Yu, Shenzhen (CN); Shiming Ai, Shenzhen (CN); Zhanxiao Yang, Shenzhen (CN); Peitao Chen, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD, Shenzhen (CN)

( * ) Notice: Subject to any disclaimer, the term of this patent is extended or adjusted under 35 U.S.C. 154(b) by 868 days.

(21) Appl. No.: 17/169,526

(22) Filed: Feb. 7, 2021

(65) Prior Publication Data
US 2021/0154428 A1     May 27, 2021

Related U.S. Application Data

(63) Continuation of application No. PCT/CN2018/101162, filed on Aug. 17, 2018.

(51) Int. Cl.
*A61M 16/10* (2006.01)
*A61M 16/00* (2006.01)

(52) U.S. Cl.
CPC .... *A61M 16/1005* (2014.02); *A61M 16/0003* (2014.02); *A61M 2016/1025* (2013.01); *A61M 2205/33* (2013.01)

(58) Field of Classification Search
CPC .. A61M 2016/1025; A61M 2202/0208; A61M 2205/33; A61M 16/1005;
(Continued)

(56) References Cited

U.S. PATENT DOCUMENTS

| | | | |
|---|---|---|---|
| 6,581,595 B1 | 6/2003 | Murdock | |
| 7,975,524 B2 * | 7/2011 | Sakai | G01N 27/4175 73/1.06 |

(Continued)

FOREIGN PATENT DOCUMENTS

| | | |
|---|---|---|
| CN | 102256649 A | 11/2011 |
| CN | 103908722 A1 | 7/2014 |

(Continued)

OTHER PUBLICATIONS

WO 2017080884 English translation (Year: 2017).*
(Continued)

*Primary Examiner* — Samchuan C Yao
*Assistant Examiner* — Sara K Toich
(74) *Attorney, Agent, or Firm* — BAYES PLLC

(57) ABSTRACT

The disclosure provides a ventilation apparatus. The ventilation apparatus includes a housing, an inhalation branch, a control unit, a gas source port, an exhalation branch, and a paramagnetic oxygen sensor. The paramagnetic oxygen sensor is used for detecting the oxygen content in the inhalation branch. The gas source port is disposed on the housing. The inhalation branch, the control unit, and the exhalation branch are enclosed within the housing. The paramagnetic oxygen sensor is disposed outside the housing.

19 Claims, 13 Drawing Sheets

(58) Field of Classification Search
CPC ............ A61M 16/085; A61M 16/1025; A61M 16/0003; A61B 5/4818; A61B 5/083; A61B 5/087
See application file for complete search history.

(56) References Cited

U.S. PATENT DOCUMENTS

| | | | |
|---|---|---|---|
| 2002/0136662 A1* | 9/2002 | Myrick | B01F 23/23413 422/45 |
| 2003/0209246 A1* | 11/2003 | Schroeder | A61M 16/1075 128/204.17 |
| 2007/0084265 A1 | 4/2007 | Haveri | |
| 2009/0272205 A1* | 11/2009 | Brown | G01L 19/0015 73/866.5 |
| 2010/0139659 A1 | 6/2010 | von Blumenthal | |
| 2016/0256656 A1 | 9/2016 | Glenn et al. | |
| 2020/0197651 A1* | 6/2020 | Glenn | A61M 16/024 |

FOREIGN PATENT DOCUMENTS

| | | | | |
|---|---|---|---|---|
| CN | 204106778 U | * | 1/2015 | |
| CN | 105628075 A | | 6/2016 | |
| CN | 105641788 A | | 6/2016 | |
| CN | 106345021 A | | 1/2017 | |
| CN | 108348715 A | | 7/2018 | |
| EP | 1775582 A1 | | 4/2007 | |
| EP | 2123320 A1 | | 11/2009 | |
| EP | 2515105 A1 | | 10/2012 | |
| JP | 2002011100 A | | 1/2002 | |
| WO | 03081225 A1 | | 10/2003 | |
| WO | WO-2017080884 A1 | * | 5/2017 | ........ A61M 16/0003 |

OTHER PUBLICATIONS

CN 204106778 U English translation (Year: 2015).*
International Search Report issued in corresponding International Application No. PCT/CN2018/101162, mailed May 6, 2019, 4 pages.
Communication pursuant to Article 94(3) EPC issued in related European Application No. 18930080.9, mailed Oct. 12, 2021, 4 pages.
First Office issued in related Chinese Application No. 201880093627.2, mailed Feb. 18, 2022, 8 pages.
Extended European Search Report issued in related European Application No. 18930080.9, mailed Jul. 27, 2021, 8 bages.

* cited by examiner

VENTILATION APPARATUS

CROSS-REFERENCE TO RELATED APPLICATIONS

This application is a bypass continuation of Patent Cooperation Treaty Application No. PCT/CN2018/101162 filed Aug. 17, 2018, the content of which is incorporated herein by reference in its entirety.

TECHNICAL FIELD

The disclosure relates to the technical field of medical instruments, and in particular, relates to a ventilation apparatus.

BACKGROUND

An oxygen concentration sensor is an important part of a ventilator. The ventilator monitors, by means of the oxygen concentration sensor, an oxygen concentration value of a mixed gas conveyed to a patient by the ventilator. At present, a chemical oxygen battery is mainly used as the oxygen concentration sensor for the ventilator.

The chemical oxygen battery is widely used due to its low cost, but the chemical oxygen battery needs to consume an internal lead electrode during measurement, has a service life of only 1-2 years, and needs to be replaced regularly. If the chemical oxygen battery is used for a long time and exceeds the service life, but the hospital does not replace the chemical oxygen battery on time, inaccurate monitoring of the oxygen concentration value and other consequences may be caused, which may pose a risk to the patient. In addition, the chemical oxygen battery is usually disposed inside the ventilator, resulting in inconvenient maintenance.

SUMMARY

The disclosure provides a ventilation apparatus. On one hand, the service life may be prolonged, the detection precision may be improved, and the risk to a patient is avoided; and on the other hand, a paramagnetic oxygen sensor is convenient to maintain.

In order to achieve this objective, the disclosure employs the following technical solution:
  a ventilation apparatus, including a housing, a gas source port disposed on the housing, and an inhalation branch, an exhalation branch and a control unit enclosed within the housing, where the ventilation apparatus further includes a mounting assembly and a paramagnetic oxygen sensor disposed outside the housing by means of the mounting assembly, the paramagnetic oxygen sensor detecting oxygen content in the inhalation branch.

In an embodiment, a gas inlet of the paramagnetic oxygen sensor is connected to the inhalation branch by means of an adapter tube or a sampling tube.

In an embodiment, the adapter tube and the mounting assembly are integrated.

In an embodiment, the ventilation apparatus further includes:
  a buffer structure at least partially disposed outside the paramagnetic oxygen sensor.

In an embodiment, the buffer structure includes:
  a buffer cover sleeving at least part of a periphery of the paramagnetic oxygen sensor.

In an embodiment, the buffer structure includes: a buffer pad,
  where the buffer pad is:
    at least partially disposed between the housing and the paramagnetic oxygen sensor; or
    at least partially disposed between the inhalation branch and the paramagnetic oxygen sensor; or
    partially disposed between the housing and the paramagnetic oxygen sensor and partially disposed between the inhalation branch and the paramagnetic oxygen sensor.

In an embodiment, a gas inlet of the paramagnetic oxygen sensor is connected to the inhalation branch by means of the adapter tube, and the buffer pad sleeves a periphery of the adapter tube.

In an embodiment, a mounting groove is disposed in the periphery of the adapter tube, and the buffer pad is disposed in the mounting groove.

In an embodiment, at least part of a periphery of the buffer pad is serrated.

In an embodiment, the buffer pad is disposed with a plurality of through holes.

In an embodiment, the buffer structure includes:
  a buffer connecting member, the paramagnetic oxygen sensor being movably connected to the housing by means of the buffer connecting member.

In an embodiment, the buffer connecting member includes a sliding portion, the paramagnetic oxygen sensor being movable relative to the sliding portion.

In an embodiment, the ventilation apparatus further includes:
  a mounting error prevention structure for properly mounting the paramagnetic oxygen sensor on the housing in a preset direction.

In an embodiment, the ventilation apparatus further includes:
  a shielding structure matching the housing to jointly accommodate the paramagnetic oxygen sensor.

In an embodiment, the ventilation apparatus further includes an outer cover, the paramagnetic oxygen sensor being disposed inside the outer cover, and the outer cover being connected to the housing.

The ventilation apparatus disposed by the disclosure includes the housing, the inhalation branch, the control unit, the gas source port, the exhalation branch, and the paramagnetic oxygen sensor. The paramagnetic oxygen sensor is used for detecting the oxygen content in the inhalation branch, and the paramagnetic oxygen sensor is basically free of loss during measurement, so that the service life may be prolonged, the condition of inaccurate detection precision caused by untimely replacement after long-term use is avoided, safety of the ventilation apparatus during use is ensured, and the risk to the patient is avoided. Moreover, the gas source port is disposed on the housing, the inhalation branch, the control unit and the exhalation branch are enclosed within the housing, the paramagnetic oxygen sensor is disposed outside the housing, and an operator may maintain the paramagnetic oxygen sensor without dismounting the housing, thereby facilitating maintenance of the paramagnetic oxygen sensor.

Figure 1:
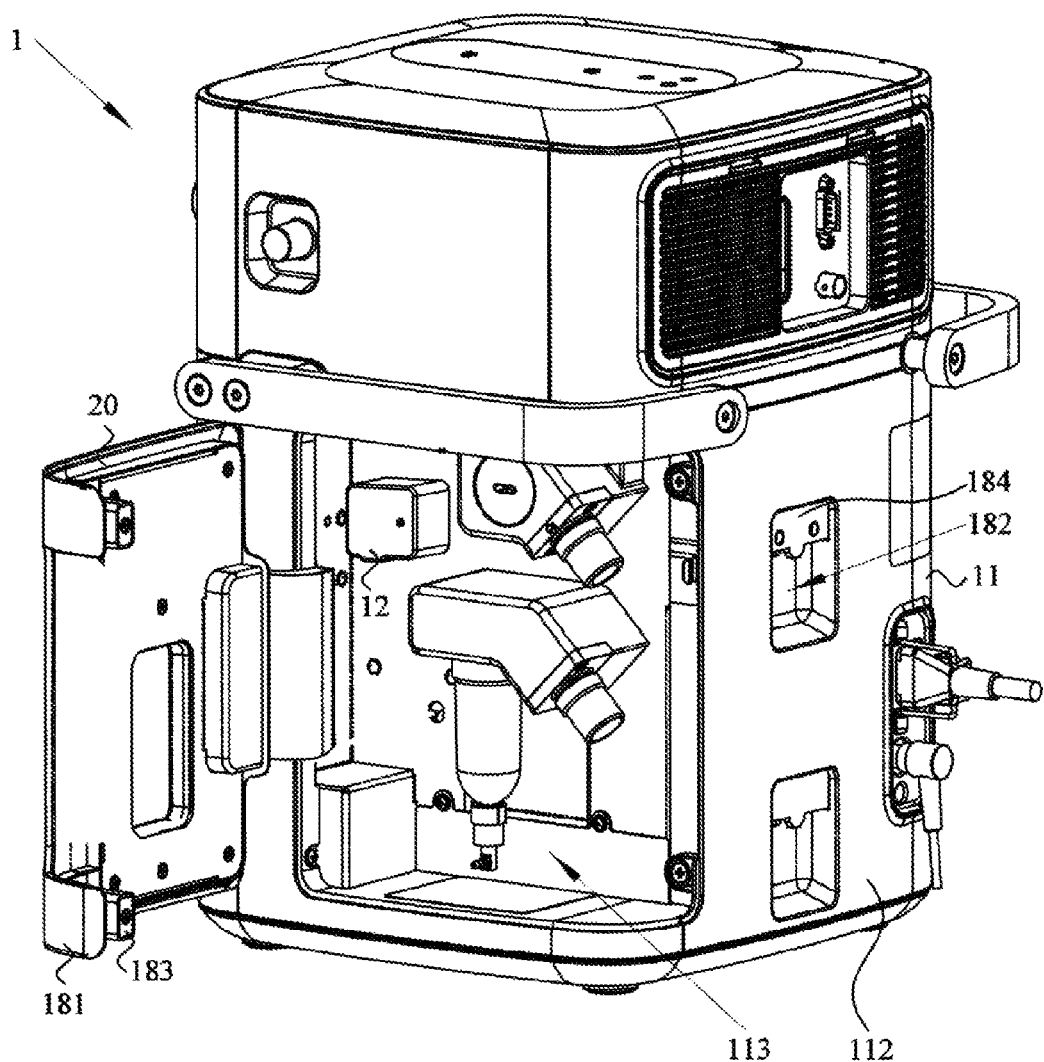
FIG. 1 is a schematic structural diagram of a ventilation apparatus provided by an embodiment of the disclosure.

Reference numerals in the accompanying drawings are as follows:

1—Ventilation apparatus;
11—Housing; 12—Paramagnetic oxygen sensor; 13—Buffer structure; 15—Outer cover; 16—Inhalation branch; 17—Control unit; 18—Gas source port; 19—Exhalation branch; 20—Mounting door; 21—Paramagnetic oxygen adapter block;
111—Mounting hole; 112—Body; 113—Mounting groove; 122—Paramagnetic oxygen sensor body; 131—Buffer connecting member; 132—Buffer pad; 133—Buffer cover; 141—First positioning set; 142—Second positioning set; 181—Hook; 182—Hanging groove; 183—First electromagnetic assembly; 184—Second electromagnetic assembly; 211—Adapter tube;
1221—Sensor Housing; 1222—First magnetic pole; 1223—Second magnetic pole; 1224—First hollow sphere; 1225—Second hollow sphere; 1226—Metal band; 1227—Planar mirror; 1228—Photocell; 1229—Light source assembly; 1230—Controller; 1231—Amplifier; 1311—Sliding portion; 1312—Connector; 1313—Threaded portion; 1321—First buffer portion; 1322—Second buffer portion; 1323—Through hole; 1331—Protrusion; 1411—First positioning column; 1412—First positioning hole; 1421—Second positioning hole; 1422—Third positioning hole; 2111—Mounting groove;
12211—Gas inlet; 12212—Gas outlet; 12213—Gas channel.

DETAILED DESCRIPTION

In order to enable those skilled in the art to better understand the technical solutions of the embodiments of the disclosure, the technical solutions of the embodiments of the disclosure are further described below in conjunction with the accompanying drawings and through the description of the disclosed embodiments.

Figure 2:
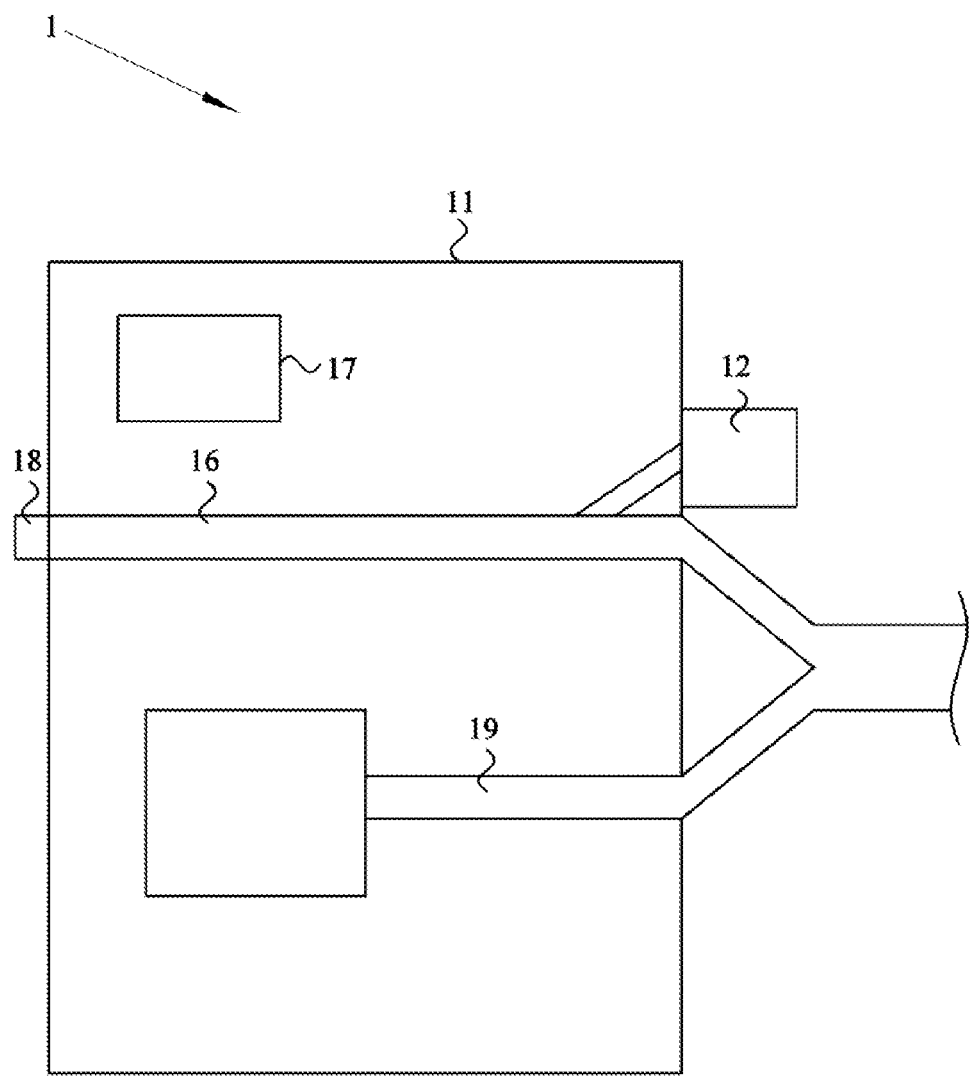
FIG. 2 is a simplified diagram of an interior of the ventilation apparatus provided by an embodiment of the disclosure.
Figure 3:
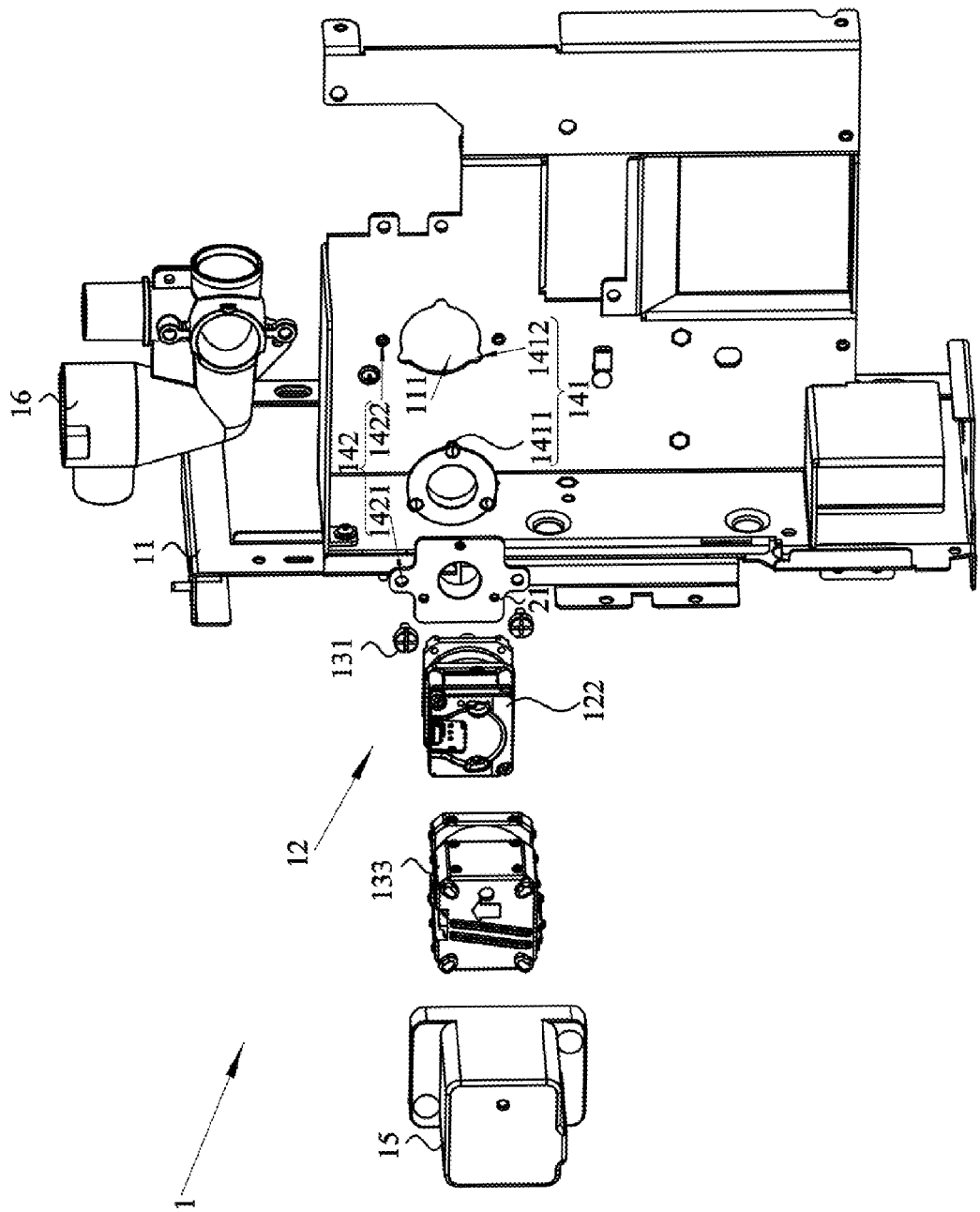
FIG. 3 is an exploded view, in one direction, of the ventilation apparatus provided by an embodiment of the disclosure.

FIG. 1 is a schematic structural diagram of a ventilation apparatus 1 provided by an embodiment of the disclosure. FIG. 2 is a simplified diagram of an interior of the ventilation apparatus 1 provided by an embodiment of the disclosure. FIG. 3 is an exploded view, in one direction, of the ventilation apparatus 1 provided by an embodiment of the disclosure. As shown in FIGS. 1-3, the ventilation apparatus 1 provided by an embodiment of the disclosure includes a housing 11, an inhalation branch 16, a control unit 17, a gas source port 18, an exhalation branch 19, and a paramagnetic oxygen sensor 12. The paramagnetic oxygen sensor 12 is configured to detect oxygen content in the inhalation branch 16, and the paramagnetic oxygen sensor 12 is basically free of loss during measurement, so that the service life may be prolonged, the condition of inaccurate detection precision caused by untimely replacement after long-term use is avoided, the safety of the ventilation apparatus 1 during use is ensured, and the risk to a patient is avoided. Moreover, the gas source port 18 is disposed on the housing 11, the inhalation branch 16, the control unit 17 and the exhalation branch 19 are enclosed within the housing 11, the paramagnetic oxygen sensor 12 is disposed outside the housing 11 by means of a mounting assembly, for example, a screw, a snap-fit fastener, etc., and an operator may maintain the paramagnetic oxygen sensor 12 without dismounting the housing 11, thereby facilitating maintenance of the paramagnetic oxygen sensor 12. The ventilation apparatus 1 provided by the embodiment of the disclosure may be a ventilator, an anesthesia machine, etc.

As shown in FIG. 2, the gas source port 18 in the embodiment of the disclosure is in communication with the inhalation branch 16, and the inhalation branch 16 and the exhalation branch 19 are connected to a mouth and a nose of the patient by means of a patient pipeline. When the patient inhales, gas introduced from the gas source port 18 is transmitted to the mouth and the nose of the patient by means of the inhalation branch 16. When the patient exhales, exhaled gas is exhausted by means of the exhalation branch 19. The control unit 17 may control opening and closing of the inhalation branch 16 and the exhalation branch 19 separately, thereby achieving normal use of the ventilation apparatus 1.

An area outside the housing 11 referred to in the embodiment of the disclosure refers to a spatial area between the housing and an area outside the interior where the inhalation branch 16 is disposed. In an embodiment, as shown in FIG. 1, the housing 11 provided by the embodiment of the disclosure includes a body 112 and a mounting groove 113, and the paramagnetic oxygen sensor 12 is disposed in the mounting groove 113, which may effectively reduce an overall size of the ventilation apparatus 1. Besides, the ventilation apparatus 1 provided by the embodiment of the disclosure further includes a mounting door 20, the mounting door 20 covers an opening position of the mounting groove 113, one side of the mounting door 20 is hinged to the body 112, a hook 181 is disposed on the other side of the mounting door 20, a hanging groove 182 is disposed in the body 112, and when the hook 181 is hung in the hanging groove 182, the mounting door 20 and the body 112 may be locked, so that the effect of shielding the paramagnetic oxygen sensor 12 is achieved, and an appearance of the ventilation apparatus 1 may be more attractive. A first electromagnetic assembly 183 is disposed on the hook 181, a second electromagnetic assembly 184 is disposed in the hanging groove 182, the first electromagnetic assembly 183 and the second electromagnetic assembly 184 are connected to a power source separately, and when at least one of the first electromagnetic assembly 183 and the second electromagnetic assembly 184 is energized, attraction of the first electromagnetic assembly 183 and the second electromagnetic assembly 184 may be achieved, thereby further improving secure locking between the mounting door 20 and the body 112. When the paramagnetic oxygen sensor 12 needs to be maintained or inspected, only the mounting door 20 needs to be opened, which is simple and convenient. Of course, latches, screws and other locking structures may also be disposed between the mounting door 20 and the body 112 of the housing 11 to lock the mounting door 20 to the body 112 after the mounting door is closed. In the embodiment of the disclosure, the housing 11, referring to a housing part that needs to be dismounted by service personnel with a tool, of the ventilation apparatus is referred to as "housing". In an embodiment, the mounting door 20 may also be replaced with other shielding structures to match the housing 11 to jointly accommodate the paramagnetic oxygen sensor 12.

In an embodiment, it is also possible that only the body 112 is disposed with the mounting groove 113, and the paramagnetic oxygen sensor 12 is entirely or partially accommodated in the mounting groove 113. In an embodiment, it is also possible that only the paramagnetic oxygen sensor 12 is disposed on an outer surface of the body 112, and no mounting door 20 is additionally provided, thereby facilitating mounting of the paramagnetic oxygen sensor 12; and it is also possible that the paramagnetic oxygen sensor 12 is directly mounted outside the housing 11 by means of the mounting assembly, and no mounting groove 113 and no mounting door 20 are provided.

In an embodiment, the mounting door 20 and the body 112 may also be locked by means of other easily-removable locking structures, for example, hook structures, etc., all of which fall within the scope of protection of the application.

Figure 4:
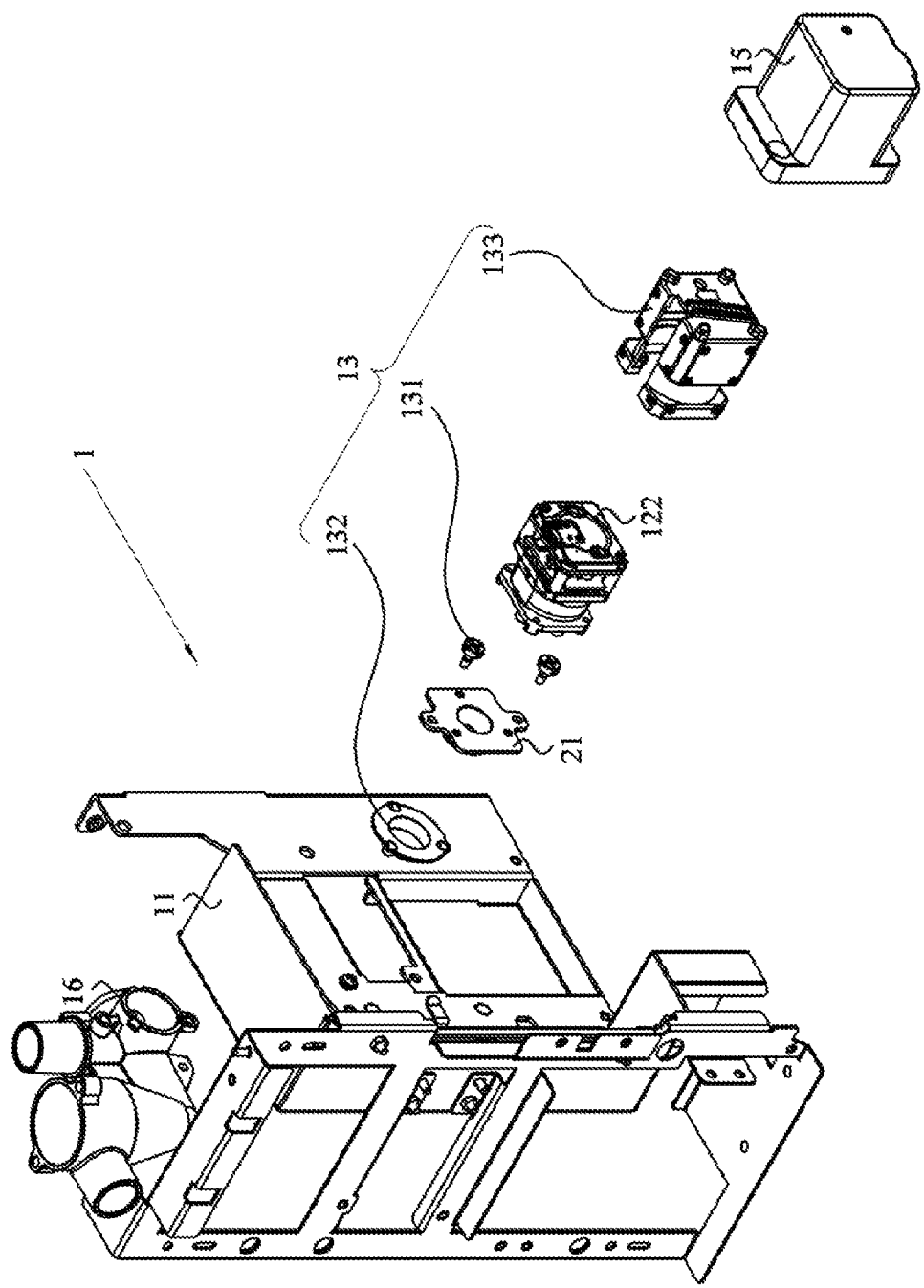
FIG. 4 is an exploded view, in another direction, of the ventilation apparatus provided by an embodiment of the disclosure.

FIG. 4 is an exploded view, in another direction, of the ventilation apparatus 1 provided by an embodiment of the disclosure. As shown in FIG. 3 and FIG. 4, the ventilation apparatus 1 provided by the embodiment of the disclosure further includes a buffer structure 13, a mounting error prevention structure and an outer cover 15.

Figure 5:
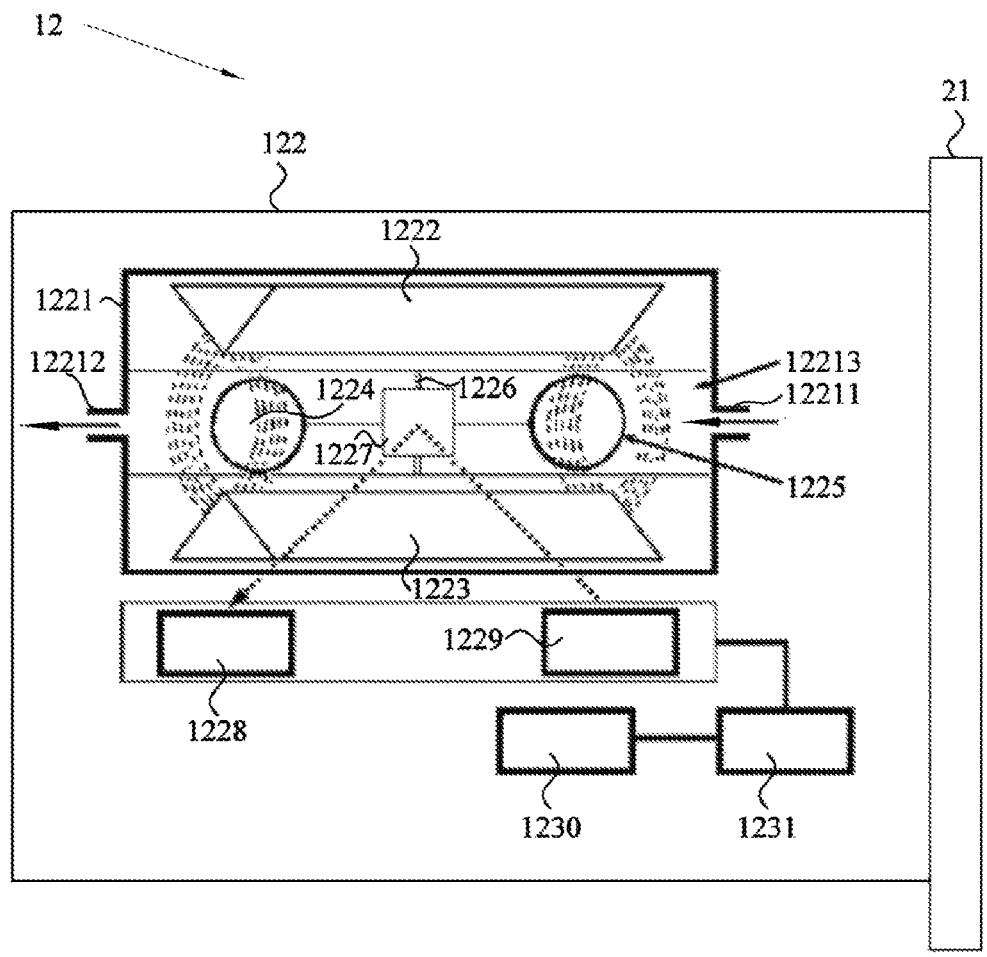
FIG. 5 is a simplified diagram of a structure of a paramagnetic oxygen sensor provided by an embodiment of the disclosure.

Various parts are described below in conjunction with other accompanying drawings:

FIG. 5 is a simplified diagram of a structure of the paramagnetic oxygen sensor 12 provided by an embodiment of the disclosure. As shown in FIG. 5, the paramagnetic oxygen sensor 12 provided by the embodiment of the disclosure includes a paramagnetic oxygen sensor body 122, where the paramagnetic oxygen sensor body 122 includes a sensor housing 1221, a first magnetic pole 1222, a second magnetic pole 1223, a first hollow sphere 1224, a second hollow sphere 1225, a metal band 1226, a planar mirror 1227, a photocell 1228, a light source assembly 1229, a controller 1230, and an amplifier 1231. A gas inlet 12211, a gas outlet 12212 and a gas channel 12213 are disposed in the sensor housing 1221, the gas inlet 12211 and the gas outlet 12212 are located at two ends of the gas channel 12213 respectively, gradients of magnetic field intensities of the first magnetic pole 1222 and the second magnetic pole 1223 are opposite, and the first magnetic pole and the second magnetic pole are disposed in the sensor housing 1221. The metal band 1226 is disposed on the sensor housing 1221, the first hollow sphere 1224 and the second hollow sphere 1225 which are equal in volume are disposed in the gas channel 12213 by means of the metal band 1226, the first hollow sphere 1224 and the second hollow sphere 1225 are disposed in a gap between the first magnetic pole 1222 and the second magnetic pole 1223, and the first hollow sphere 1224 and the second hollow sphere 1225 rotate with the metal band 1226 as an axis of rotation but may not swing vertically. The planar mirror 1227 is disposed at an intersection point of a connecting line of the first hollow sphere 1224 and the second hollow sphere 1225 and the metal band 1226, the controller 1230 enables the light source assembly 1229 to emit a light ray by means of the amplifier 1231, and the emitted light ray irradiates the mirror 1227 and then is reflected to the photocell 1228. When measured gas enters the gas channel 12213 from the gas inlet 12211, paramagnetic gas molecules (oxygen molecules) contained in the gas are attracted by a magnetic field to get close to the magnetic field. Due to the attraction of a non-uniform magnetic field to the paramagnetic gas molecules (oxygen molecules), a molecular density of an area close to the magnetic field intensity is relatively high, and a pressure difference in direct proportion to the oxygen content is generated in a gradient direction of the magnetic field intensity, such that the first hollow sphere 1224 and the second hollow sphere 1225 generate a thrust due to the pressure difference, and the thrust makes the first hollow sphere 1224 and the second hollow sphere 1225 deflect at an angle. Meanwhile, the planar mirror 1227 also deflects, thereby making irradiation received by the photocell 1228 change, and then an electric signal is generated, where the electric signal is in direct proportion to the deflection angle of the first hollow sphere 1224 and the second hollow sphere 1225 and is in direct proportion to the oxygen content in the measured gas. The paramagnetic oxygen sensor 12 uses physical characteristics of oxygen, and the paramagnetic oxygen sensor 12 is basically free of loss during measurement, so the paramagnetic oxygen sensor 12 is long in service life and may be free of replacement in an entire life cycle of the ventilation apparatus 1, the problem of inaccurate precision after long-term use of a chemistry oxygen battery is avoided, and the safety and reliability of the ventilation apparatus 1 are improved.

Figure 6:
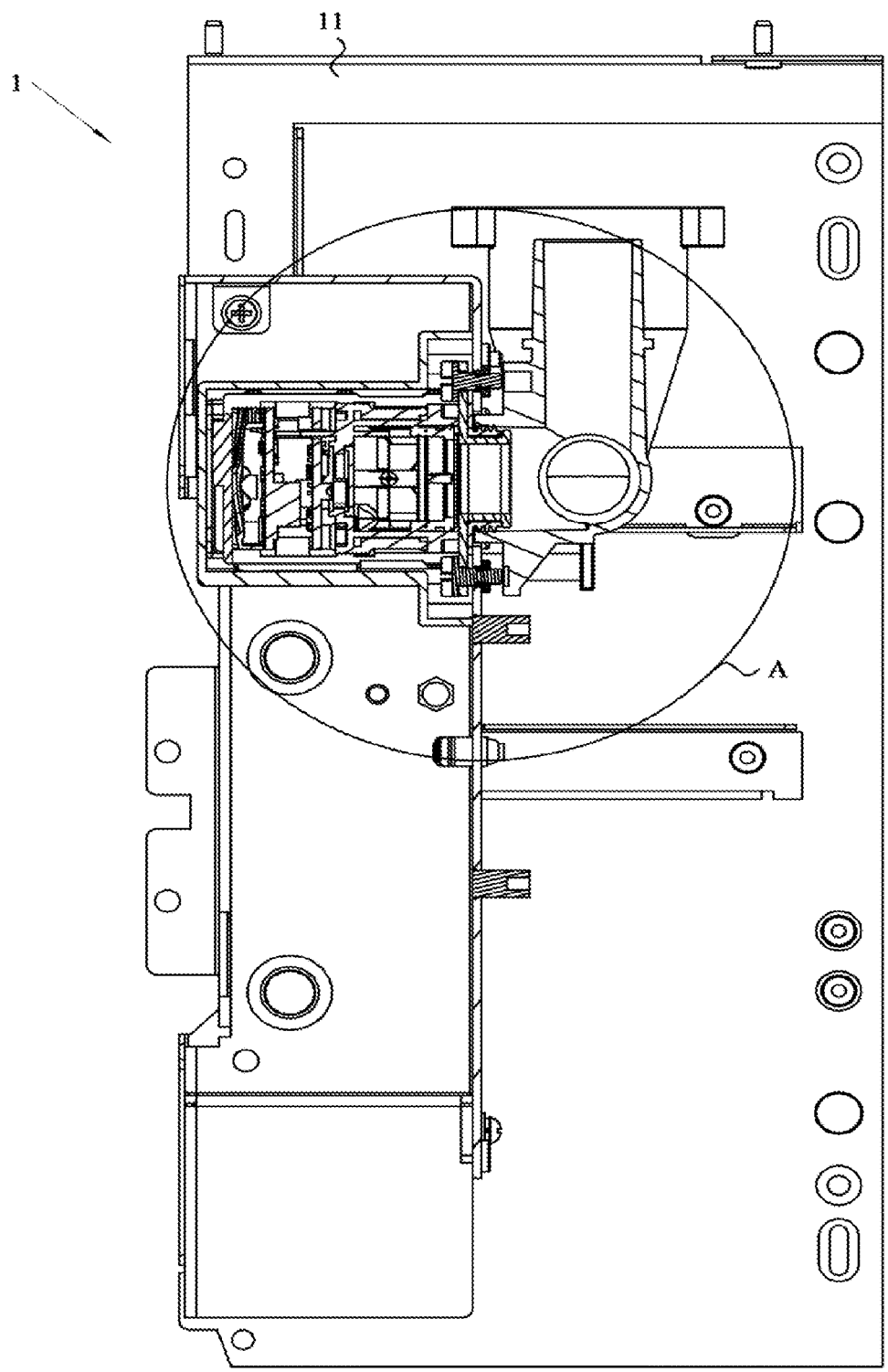
FIG. 6 is a cutaway view of the ventilation apparatus provided by an embodiment of the disclosure.
Figure 7:
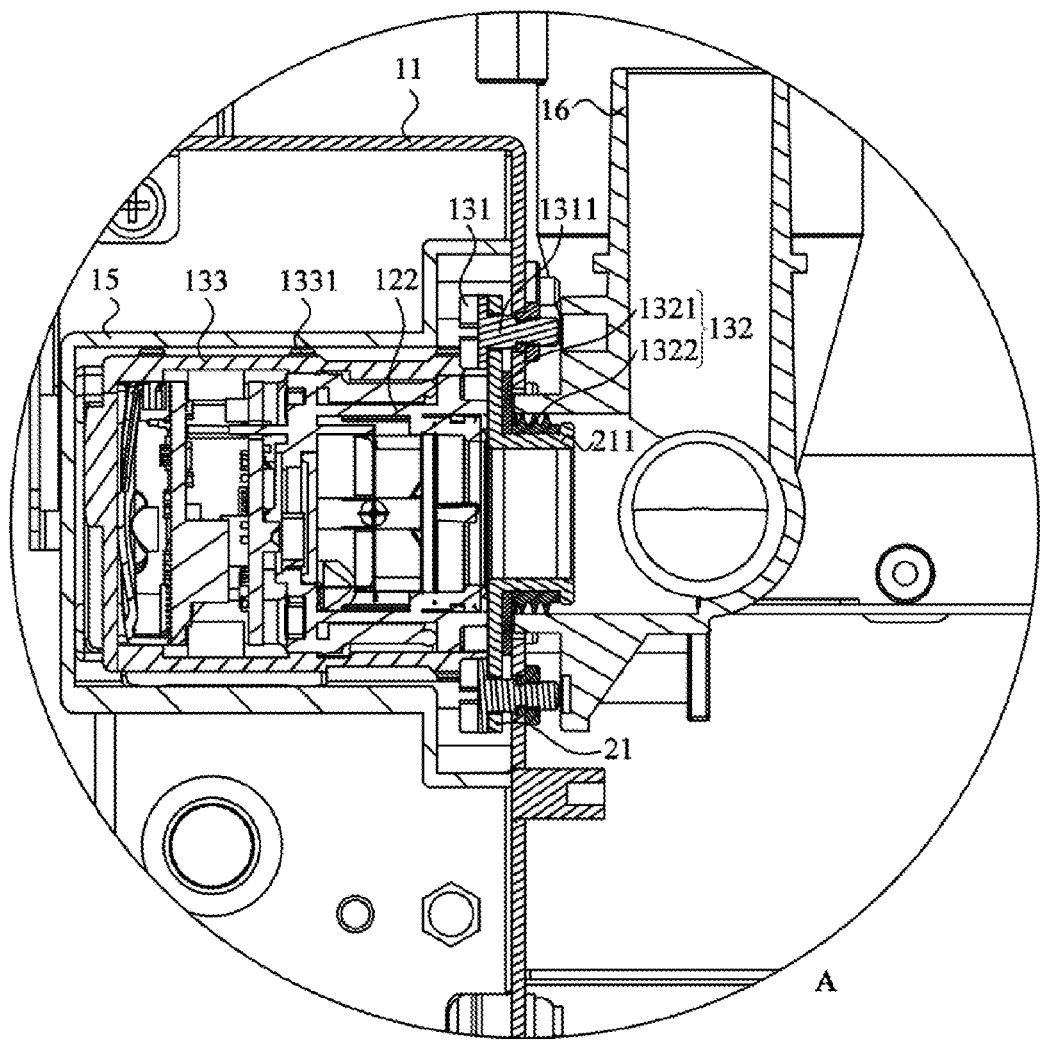
FIG. 7 is a partially enlarged diagram of portion A in FIG. 6.

Due to the facts that the ventilation apparatus 1 vibrates when working, and an interior of the paramagnetic oxygen sensor 12 is of a mechanical structure, if the paramagnetic oxygen sensor 12 is directly and fixedly connected to the housing 11, the first hollow sphere 1224, the second hollow sphere 1225 and the metal band 1226 in the paramagnetic oxygen sensor are easily affected, resulting in inaccurate oxygen concentration measurement, and even resulting in damage to an internal structure of the paramagnetic oxygen sensor 12. FIG. 6 is a cutaway view of the ventilation apparatus 1 provided by an embodiment of the disclosure, and FIG. 7 is a partially enlarged diagram of portion A in FIG. 6. As shown in FIGS. 4-7, in the embodiment of the disclosure, at least part of the buffer structure 13 is disposed outside the paramagnetic oxygen sensor 12, so that vibration transmitted into the paramagnetic oxygen sensor 12 may be effectively reduced, damage to the internal structure of the paramagnetic oxygen sensor 12 is avoided, and the accuracy of measuring the oxygen concentration by the paramagnetic oxygen sensor 12 is ensured.

In an embodiment, as shown in FIG. 7, the buffer structure 13 includes a buffer connecting member 131, and the paramagnetic oxygen sensor 12 is connected to the housing 11 by means of the buffer connecting member 131 to guarantee that the paramagnetic oxygen sensor 12 may move relative to the housing 11. The paramagnetic oxygen sensor 12 is not completely fastened to the housing 11, so a certain shaking amount exists between the paramagnetic oxygen sensor 12 and the housing 11, vibration directly transmitted to the paramagnetic oxygen sensor 12 may be reduced, and the damage to the internal structure of the paramagnetic oxygen sensor 12 is avoided.

Figure 8:
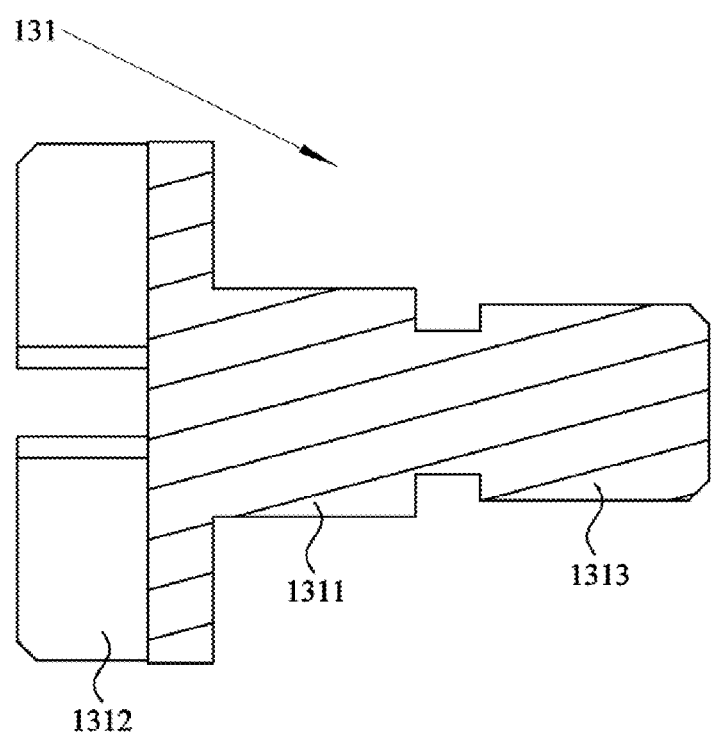
FIG. 8 is a schematic structural diagram of a buffer connecting member provided by an embodiment of the disclosure.

In an embodiment, FIG. 8 is a schematic structural diagram of the buffer connecting member 131 provided by an embodiment of the disclosure, and the buffer connecting member 131 includes a connector 1312, a sliding portion 1311, and a threaded portion 1313 connected in sequence. In combination with FIG. 8 and FIG. 7, the ventilation apparatus 1 provided by the embodiment of the disclosure further includes a paramagnetic oxygen adapter block 21, where the paramagnetic oxygen adapter block 21 movably sleeves the sliding portion 1311, and the buffer connecting member 131 is fixed to the housing 11 by means of the threaded portion 1313. In an axial direction of the buffer connecting member 131, a thickness of the paramagnetic oxygen adapter block 21 is smaller than a distance between the connector 1312 and the housing 11, so as to guarantee that the paramagnetic oxygen adapter block 21 is limited to movement between the connector 1312 and the housing 11. Besides, a connecting hole is disposed in the paramagnetic oxygen adapter block 21, the buffer connecting member 131 penetrates the connecting hole, and a diameter of the connecting hole is larger than that of the sliding portion 1311, so as to guarantee that the paramagnetic oxygen adapter block 21 may move in a radial direction relative to the buffer connecting member 131, and the paramagnetic oxygen adapter block 21 moves relative to the housing 11 in the radial direction of the buffer connecting member 131. In an embodiment, the buffer connecting member 131 and the housing 11 may also be fixed by welding or other modes.

As shown in FIG. 7, two buffer connecting members 131 are provided, distances between axes of the two buffer connecting members 131 located at different mounting positions and a center line of the mounting hole 111 are different, and when the paramagnetic oxygen adapter block 21 is mounted, a good mounting error prevention effect may be achieved, thereby guaranteeing that a mounting direction of the paramagnetic oxygen sensor 12 is correct, and achieving normal use of the paramagnetic oxygen sensor 12. In an embodiment, three, four or more buffer connecting members 131 may also be provided.

Figure 9:
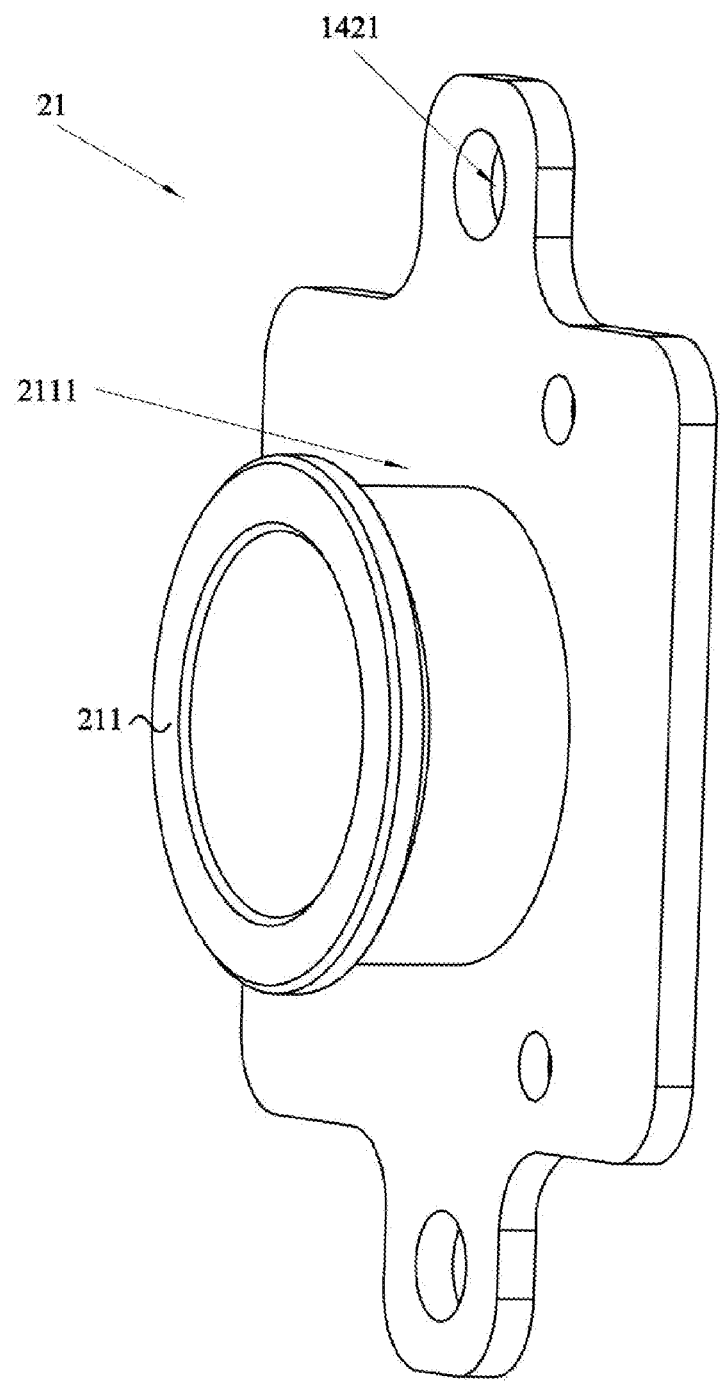
FIG. 9 is a schematic structural diagram of a paramagnetic oxygen adapter block provided by an embodiment of the disclosure.
Figure 10:
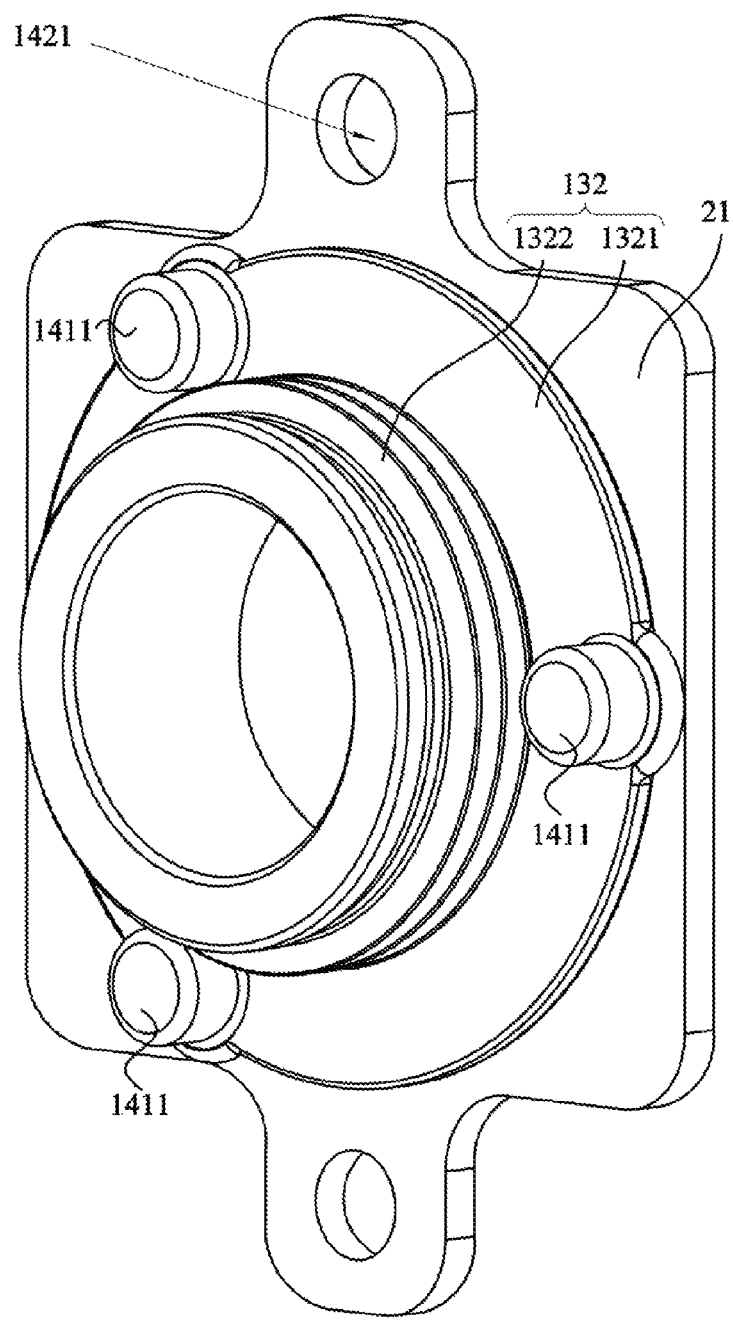
FIG. 10 is a schematic structural diagram of the paramagnetic oxygen adapter block and a buffer pad provided by an embodiment of the disclosure.

FIG. 9 is a schematic structural diagram of the paramagnetic oxygen adapter block 21 provided by an embodiment of the disclosure, and FIG. 10 is a schematic structural diagram of the paramagnetic oxygen adapter block 21 and a buffer pad 132 provided by an embodiment of the disclosure. As shown in FIGS. 7, 9, and 10, the buffer pad 132 includes a first buffer portion 1321 and a second buffer portion 1322 connected to each other, where the first buffer portion 1321 is disposed between the housing 11 and the paramagnetic oxygen sensor 12. On one hand, the first buffer portion 1321 may absorb vibration generated by movement of the paramagnetic oxygen sensor 12 relative to the housing 11 in a horizontal direction of FIG. 6; and on the other hand, the first buffer portion 1321 may absorb vibration generated from the housing 11. In an embodiment, the first buffer portion 1321 may be made of an elastic deformable material such as rubber, and when the paramagnetic oxygen adapter block 21 moves relative to the housing 11, constant sealing between the housing 11 and the paramagnetic oxygen sensor 12 may be achieved. The second buffer portion 1322 is disposed between the inhalation branch 16 and the paramagnetic oxygen sensor 12; on one hand, the second buffer portion 1322 may absorb vibration generated by movement of the paramagnetic oxygen sensor 12 relative to the inhalation branch 16 in a vertical direction of FIG. 6; and on the other hand, the second buffer portion 1322 may achieve constant sealing between the paramagnetic oxygen sensor 12 and the inhalation branch 16, prevent gas leakage, and improve a utilization rate of the ventilation apparatus 1.

In an embodiment, it is also possible to only provide the first buffer portion 1321, or the second buffer portion 1322, which may also achieve buffer and sealing effects.

As shown in FIG. 9, the paramagnetic oxygen adapter block 21 provided by the embodiment of the disclosure includes an adapter tube 211, and as shown in FIG. 4, the adapter tube 211 may extend into the mounting hole 111 in the housing 11, and the adapter tube 211 is connected to the inhalation branch 16 disposed in the housing 11, thereby achieving the effect of transmitting the gas in the ventilation apparatus 1 into the paramagnetic oxygen sensor 12. In an embodiment, the ventilation apparatus 1 further includes the mounting assembly, the paramagnetic oxygen sensor 12 may be mounted on the housing 11 by means of the mounting assembly, and the mounting assembly in the embodiment of the disclosure may include a plate body of the paramagnetic oxygen adapter block 21 and the buffer connecting member 131, where the plate body of the paramagnetic oxygen adapter block 21, the buffer connecting member 131 and the adapter tube 211 may be integrated. In an embodiment, a gas inlet of the paramagnetic oxygen sensor 12 may also be connected to the inhalation branch 16 by means of a flexible-textured sampling tube, thereby achieving the effect of transmitting the gas of the internal inhalation branch 16 of the ventilation apparatus 1 into the paramagnetic oxygen sensor 12. By arranging the mounting hole 111, the paramagnetic oxygen adapter block 21 and the housing 11 may be well positioned and mounted, thereby improving the mounting efficiency and precision of the paramagnetic oxygen sensor 12.

The adapter tube 211 provided by the embodiment of the disclosure extends into the inhalation branch 16, the second buffer portion 1322 sleeves a periphery of the adapter tube 211, and the periphery of the adapter tube 211 abuts against an inner peripheral wall of the inhalation branch 16, thereby achieving sealing between the adapter tube 211 and the inhalation branch 16. The mounting groove 2111 is disposed in the periphery of the adapter tube 211 provided by the embodiment of the disclosure, and the second buffer portion 1322 is disposed in the mounting groove 2111, so that the second buffer portion 1322 may be well mounted and positioned, and the second buffer portion 1322 is prevented from deviating during the use of the ventilation apparatus 1.

In the embodiment of the disclosure, the first buffer portion 1321 and the second buffer portion 1322 may be integrally formed, thereby simplifying an assembly process of the first buffer portion 1321 and the second buffer portion 1322 to the paramagnetic oxygen adapter block 21, and improving the mounting efficiency of the ventilation apparatus 1. In an embodiment, the first buffer portion 1321, the second buffer portion 1322 and the paramagnetic oxygen adapter block 21 may also be integrally formed, which improves the mounting efficiency of the ventilation apparatus 1.

Figure 11:
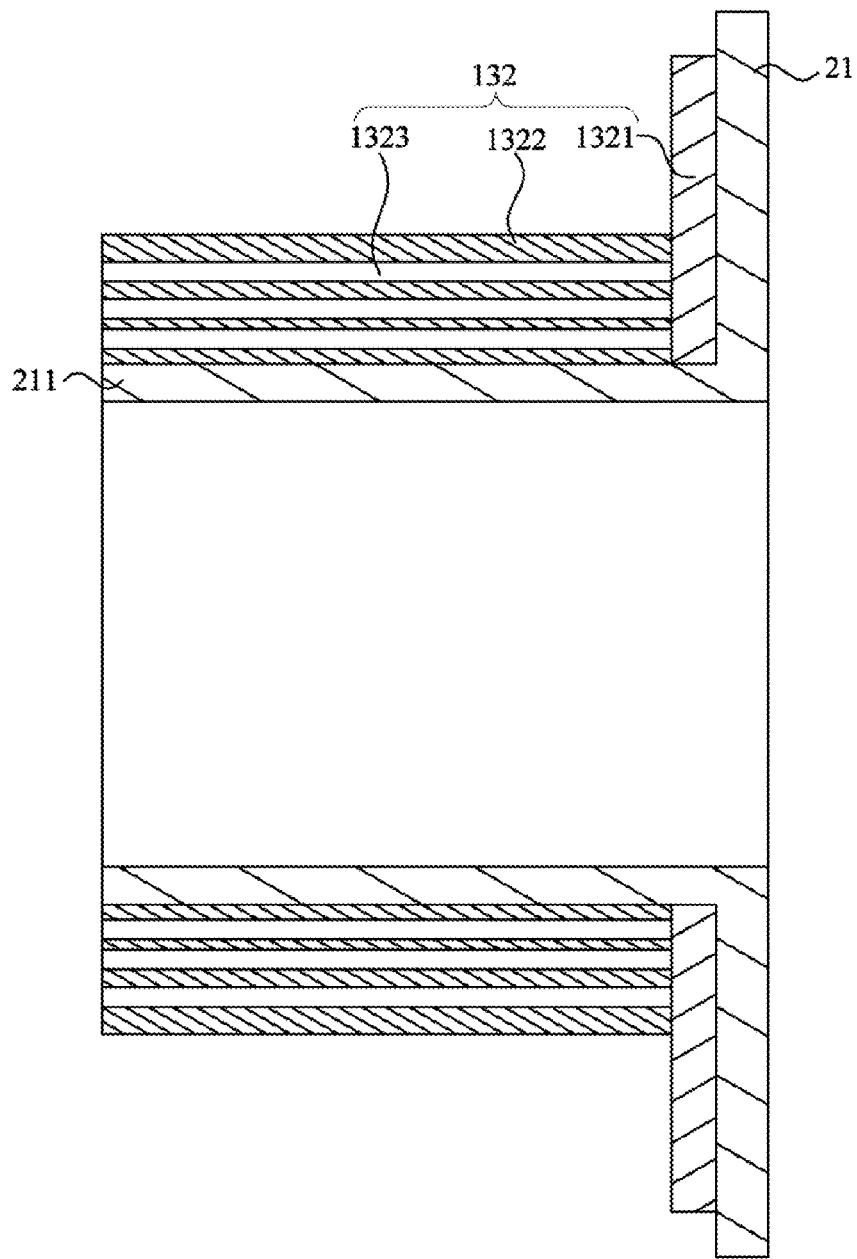
FIG. 11 is a schematic structural diagram of another paramagnetic oxygen adapter block and another buffer pad provided by an embodiment of the disclosure.

For the second buffer portion 1322, a periphery of the second buffer portion 1322 is serrated, which may further improve compressibility of the buffer pad 132, and the absorption of vibration transmitted from the housing 11 may be further improved by means of compressive deformation of the second buffer portion 1322. FIG. 11 is a schematic structural diagram of another paramagnetic oxygen adapter block 21 and another buffer pad 132 provided by other embodiments, and as shown in FIG. 11, a plurality of through holes 1323 may also be disposed in the second buffer portion 1322, which may also improve the compressibility of the second buffer portion 1322. In an embodiment, the through hole 1323 extends in a lengthwise direction of the adapter tube 211, which may improve a deformation effect of the second buffer portion 1322 in a vertical direction in FIG. 11.

As shown in FIGS. 4, 5 and 10, the ventilation apparatus 1 provided by the embodiment of the disclosure further includes a mounting error prevention structure, the mounting error prevention structure may properly mount the paramagnetic oxygen sensor 12 on the housing 11 in a preset direction, thereby guaranteeing the normal use of the paramagnetic oxygen sensor 12. In an embodiment, the mounting error prevention structure includes three first positioning sets 141 and two second positioning sets 142. The first positioning set 141 includes a first positioning column 1411 and a first positioning hole 1412, the first positioning column 1411 being disposed on the buffer pad 132, and the first positioning hole 1412 being disposed on the housing 11; and the second positioning set 142 includes a second positioning hole 1421 and a third positioning hole 1422, the second positioning hole 1421 and the third positioning hole 1422 being in one-to-one correspondence, the second positioning hole 1421 being disposed on the paramagnetic oxygen adapter block 21, and the third positioning hole 1422 being disposed on the housing 11. When the first positioning column 1411 is inserted into the corresponding first positioning hole 1412, the second positioning hole 1421 is aligned with the corresponding third positioning hole 1422, and the buffer connecting member 131 sequentially penetrates the second positioning hole 1421 and the corresponding third positioning hole 1422 to connect the paramagnetic oxygen sensor 12 to the housing 11. By means of cooperation between the first positioning set 141 and the second positioning set 142, the paramagnetic oxygen sensor 12 is mounted on the housing 11 in the preset direction. In an embodiment, the first positioning column 1411 may also be disposed on the paramagnetic oxygen sensor 12, or on both the paramagnetic oxygen sensor 12 and the buffer pad 132. In an embodiment, one, two or more first positioning sets 141 may also be provided, and one, three or more second positioning sets may also be provided. In addition, the positions of the first positioning column 1411 and the first positioning hole 1412 may be interchanged, and the positions of the second positioning hole 1421 and the third positioning hole 1422 may be interchanged. In an embodiment, a mounting error prevention effect may also be achieved by means of a shape fit. In an embodiment, three first positioning sets 141 may be provided, shapes of the first positioning column 1411 and the first positioning hole 1412 of one of the first positioning sets 141 are different from those of the other two positioning sets, so as to achieve the mounting error prevention effect.

Figure 12:
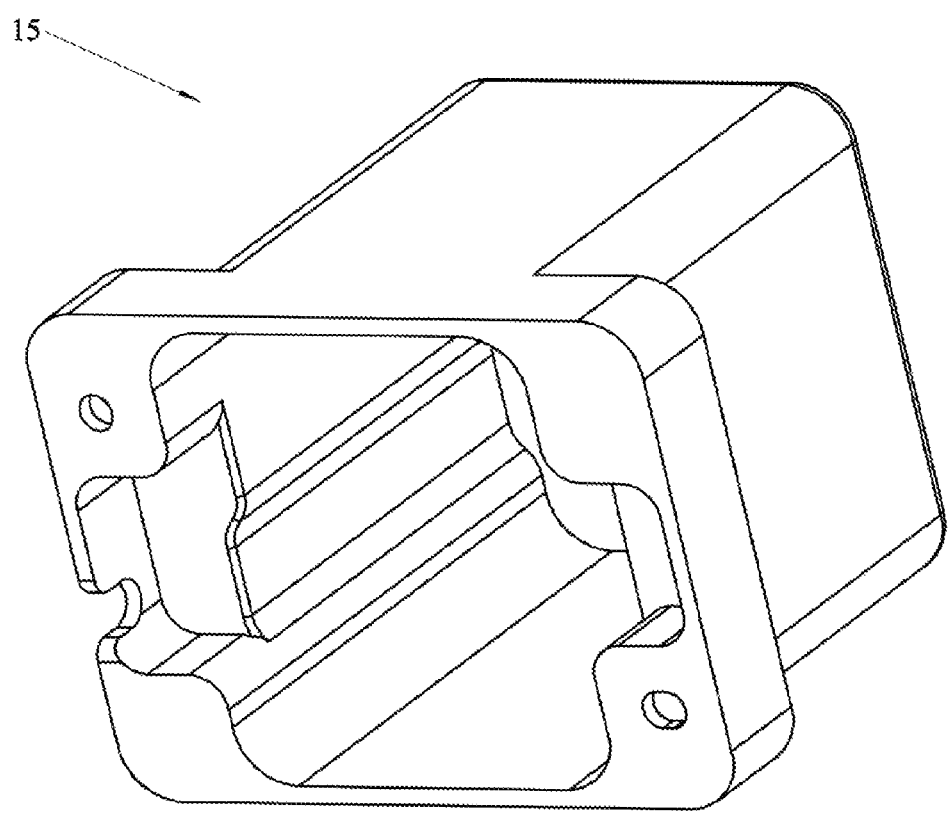
FIG. 12 is a schematic structural diagram of an outer cover provided by an embodiment of the disclosure.

FIG. 12 is a schematic structural diagram of the outer cover 15 provided by an embodiment of the disclosure. As shown in FIGS. 7 and 12, the paramagnetic oxygen sensor 12 is disposed in the outer cover 15, and the outer cover 15 is fixed to the housing 11, thereby achieving the effect of protecting the paramagnetic oxygen sensor 12, preventing external dust from entering the paramagnetic oxygen sensor 12, and guaranteeing normal use of the paramagnetic oxygen sensor 12. In an embodiment, the outer cover 15 may be made of metal and may also play a role in shielding the paramagnetic oxygen sensor 12, thereby guaranteeing that the paramagnetic oxygen sensor 12 is free of interference from external signals when working.

Figure 13:
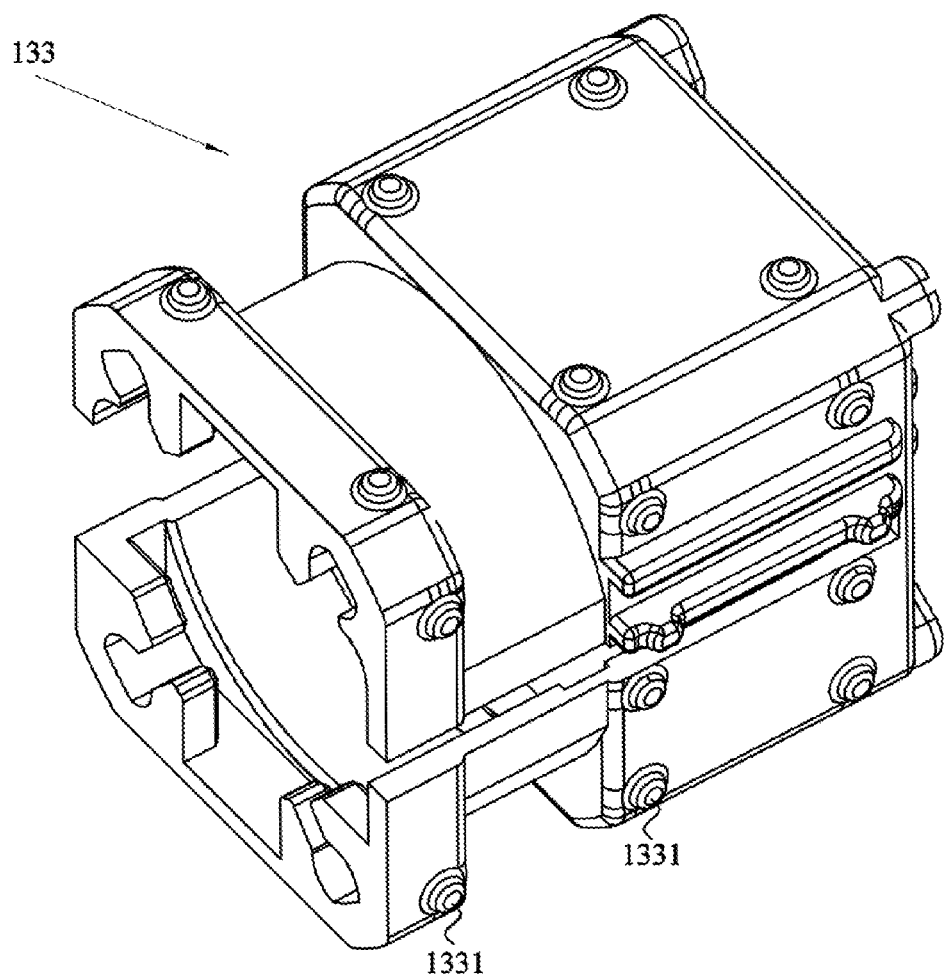
FIG. 13 is a schematic structural diagram of a buffer cover provided by an embodiment of the disclosure.

FIG. 13 is a schematic structural diagram of the buffer cover 133 provided by an embodiment of the disclosure, and as shown in FIGS. 7 and 13, the buffer cover 133 sleeves a part of the periphery of the paramagnetic oxygen sensor 12 and abuts against the outer cover 15. The outer cover 15 is fixedly connected to the housing 11, and vibration of the housing 11 is absorbed by the buffer cover 133 by means of the outer cover 15, thereby further reducing vibration borne by the paramagnetic oxygen sensor 12, and avoiding damage to the internal structure of the paramagnetic oxygen sensor 12. In an embodiment, it is also possible that peripheral surfaces of the paramagnetic oxygen sensor 12 are completely covered by the buffer cover 133, so that the effect of better reducing the vibration borne by the paramagnetic oxygen sensor 12 may be achieved.

In an embodiment, as shown in FIG. 13, a plurality of protrusions 1331 are disposed on a periphery of the buffer cover 133, such that the buffer cover 133 and the outer cover 15 abut against each other more closely, thereby avoiding relative movement between the buffer cover 133 and the outer cover 15, and improving capacity to absorb vibration by the buffer cover 133. In addition, the outer cover 15 and the buffer cover 133 may be integrally formed of rubber, thereby reducing assembly steps of the ventilation apparatus 1 and improving the mounting efficiency of the ventilation apparatus 1.

In an embodiment, it is also possible to only provide a buffer cover 133 without arranging the outer cover 15, the buffer cover 133 covers at least one surface of the paramagnetic oxygen sensor 12, and the buffer cover 133 is connected to the housing 11, such that the buffer cover 133 may absorb part of vibration transmitted from the housing 11 and may also achieve the effect of avoiding damage to the internal structure of the paramagnetic oxygen sensor 12.

What is claimed is:

1. A ventilation apparatus, comprising a housing, a gas source port disposed on the housing, an inhalation branch, an exhalation branch, and a control unit, wherein:
   the inhalation branch, the exhalation branch, and the control unit are enclosed within the housing;
   the ventilation apparatus further comprises a paramagnetic oxygen sensor disposed outside the housing, and the paramagnetic oxygen sensor is configured to detect oxygen content in the inhalation branch; and
   the paramagnetic oxygen sensor is configured to slide relative to the housing when the housing vibrates and when the paramagnetic oxygen sensor detects the oxygen content.

2. The ventilation apparatus of claim 1, wherein a gas inlet of the paramagnetic oxygen sensor is connected to the inhalation branch by means of an adapter tube or a sampling tube.

3. The ventilation apparatus of claim 2, wherein:
   the ventilation apparatus further comprises a mounting assembly, the paramagnetic oxygen sensor being disposed outside the housing by means of the mounting assembly; and
   the adapter tube and the mounting assembly are integrated.

4. The ventilation apparatus of claim 1, further comprising:
   a buffer structure at least partially disposed outside the paramagnetic oxygen sensor.

5. The ventilation apparatus of claim 4, wherein the buffer structure comprises:
   a buffer cover configured to sleeve at least part of a periphery of the paramagnetic oxygen sensor.

6. The ventilation apparatus of claim 4, wherein the buffer structure comprises a buffer pad,
wherein the buffer pad is:
at least partially disposed between the housing and the paramagnetic oxygen sensor; or
at least partially disposed between the inhalation branch and the paramagnetic oxygen sensor; or
partially disposed between the housing and the paramagnetic oxygen sensor and partially disposed between the inhalation branch and the paramagnetic oxygen sensor.

7. The ventilation apparatus of claim 6, wherein a gas inlet of the paramagnetic oxygen sensor is connected to the inhalation branch by means of an adapter tube, and the buffer pad is configured to sleeve a periphery of the adapter tube.

8. The ventilation apparatus of claim 4, wherein the buffer structure comprises:
a buffer connecting member, the paramagnetic oxygen sensor being configured to slide relative to the housing by means of the buffer connecting member when the housing vibrates.

9. The ventilation apparatus of claim 8, wherein the buffer connecting member comprises a sliding portion, the paramagnetic oxygen sensor being movable relative to the sliding portion.

10. The ventilation apparatus of claim 1, further comprising:
a mounting error prevention structure configured for mounting the paramagnetic oxygen sensor on the housing in a preset direction.

11. The ventilation apparatus of claim 1, wherein the ventilation apparatus further comprises:
a shielding structure matching the housing to jointly accommodate the paramagnetic oxygen sensor.

12. The ventilation apparatus of claim 1, further comprising an outer cover, the paramagnetic oxygen sensor being disposed inside the outer cover, and the outer cover being connected to the housing, the paramagnetic oxygen sensor being configured to slide relative to the outer cover when the housing vibrates.

13. The ventilation apparatus of claim 1, wherein the housing comprises a body and a mounting groove, and the paramagnetic oxygen sensor is disposed in the mounting groove.

14. The ventilation apparatus of claim 13, further comprising a mounting door, the mounting door covering an opening position of the mounting groove.

15. The ventilation apparatus of claim 14, wherein one side of the mounting door is hinged to the body, a hook is disposed on the other side of the mounting door, a hanging groove is disposed in the body, and when the hook is hung in the hanging groove, the mounting door and the body is locked.

16. The ventilation apparatus of claim 9, further comprising a paramagnetic oxygen adapter block, the paramagnetic oxygen adapter block movably sleeving the sliding portion.

17. The ventilation apparatus of claim 6, wherein the buffer pad comprises a first buffer portion and a second buffer portion connected to each other, the first buffer portion is disposed between the housing and the paramagnetic oxygen sensor, and the second buffer portion is disposed between the inhalation branch and the paramagnetic oxygen sensor.

18. A ventilation apparatus, comprising a housing, a gas source port disposed on the housing, an inhalation branch, an exhalation branch, and a control unit,
wherein:
the inhalation branch, the exhalation branch, and the control unit are enclosed within the housing; and
the ventilation apparatus further comprises a paramagnetic oxygen sensor disposed outside the housing, wherein the paramagnetic oxygen sensor is configured to detect oxygen content in the inhalation branch by connecting a gas inlet of the paramagnetic oxygen sensor to the inhalation branch through an adapter tube or a sampling tube, the adapter tube or the sampling tube being disposed in a mounting hole of the housing and configured to connect the inhalation branch inside the housing with the paramagnetic oxygen sensor outside the housing.

19. The ventilation apparatus of claim 18, wherein the adapter tube or the sampling tube is extended from the paramagnetic oxygen sensor into the mounting hole to connect to the inhalation branch.

* * * * *